United States Patent [19]

Uhrig et al.

[11] Patent Number: 5,266,682
[45] Date of Patent: Nov. 30, 1993

[54] NITROGEN-CONTAINING SURFACE-ACTIVE AGENTS

[75] Inventors: Heinz Uhrig, Steinbach; Siegfried Schwerin, Hofheim; Dieter Schnaitmann, Eppstein; Hans-Joachim Metz, Darmstadt, all of Fed. Rep. of Germany

[73] Assignee: Hoechst Aktiengesellschaft, Frankfurt am Main, Fed. Rep. of Germany

[21] Appl. No.: 882,695

[22] Filed: May 14, 1992

[30] Foreign Application Priority Data

May 17, 1991 [DE] Fed. Rep. of Germany ....... 4116111

[51] Int. Cl.$^5$ .............................. C09F 1/04; C08H 5/00
[52] U.S. Cl. ..................................... 530/217; 530/210; 530/211; 530/212; 530/215; 530/218; 252/8.6; 252/8.7; 524/801; 525/54.4
[58] Field of Search ................. 525/54.4; 252/8.6, 8.7; 530/210, 211, 212, 215, 217, 218; 524/801

[56] References Cited

U.S. PATENT DOCUMENTS

| | | | |
|---|---|---|---|
| 3,841,888 | 10/1974 | Belde et al. | 106/288 Q |
| 3,947,287 | 3/1976 | Belde et al. | 106/308 Q |
| 4,297,270 | 10/1981 | Uhrig et al. | 530/210 |
| 4,312,631 | 1/1982 | Cuntze et al. | 8/583 |
| 4,769,759 | 9/1988 | McGough | 364/435 |
| 4,778,919 | 10/1988 | Töpfl | 560/85 |
| 4,939,238 | 7/1990 | Uhrig et al. | 524/801 |

FOREIGN PATENT DOCUMENTS

| | | |
|---|---|---|
| 0009648 | 4/1980 | European Pat. Off. . |
| 2156603 | 2/1977 | Fed. Rep. of Germany . |
| 2236906 | 12/1979 | Fed. Rep. of Germany . |
| 3816126 | 11/1989 | Fed. Rep. of Germany . |
| 59-71486 | 4/1984 | Japan . |
| 60-24229 | 2/1985 | Japan . |

OTHER PUBLICATIONS

Ullmann's Encyclopedia of Industrial Chemistry, pp. 412–415.
J. Schreiber, Chemistry and Technology of synthetic Resinse, 5th Ed. 1943, p. 560.
Abstract of JP 58-191283 (Nikkakk) (Jun. 12, 1985).

*Primary Examiner*—Morton Foelak
*Assistant Examiner*—Richard Lee Jones

[57] ABSTRACT

The invention relates to mixtures of nitrogen-containing surface-active agents which are obtained by esterification of oxyalkylates based on modified or nonmodified naturally occurring resin acids or resin amines or resin alcohols derived therefrom with dicarboxylic acids or anhydrides thereof and subsequent reaction with alkylenediamines or alkylenepolyamines. These nitrogen-containing surface-active agents are suitable as coupling auxiliaries, emulsifiers, dispersing agents, preparation agents for solids dispersions, corrosion protection and metal-working agents and as wetting agents and dyeing auxiliaries.

23 Claims, No Drawings

NITROGEN-CONTAINING SURFACE-ACTIVE AGENTS

The invention relates to novel surface-active substances, a process for their preparation and their use.

Nonionic, anionic and also cationic surfactants are often used in the production of preparations of coloring agents, in particular pigments, for use in aqueous and organic media. Because of their surface-active properties, such surfactants have a great influence on the coloristic properties of the coloring agents in the various use media, especially in the printing sector. Surfactants are usually also used to achieve a better course of the coupling reaction in the production of azo pigments and soluble azo dyestuffs and for obtaining preparations of the coloring agents. The constantly increasing requirements imposed on the coloristic and rheological properties of the azo pigments necessitates, especially in the field of printing inks, targeted development of preparation agents which improve the flow properties of printing inks.

Esterification products of resin acids and modified resin acids with polyalcohols, for example glycerol, pentaerythritol and sorbitol, are used, for example, in the production of printing inks (Ullmann's Encyklopädie der technischen Chemie (Ullmann's Encyclopedia of Industrial Chemistry), 3rd Edition, Volume 8, page 412 and J. Scheiber, Chemie und Technologie der künstlichen Harze (Chemistry and Technology of Synthetic Resins), 5th Edition, 1943, page 560).

Oxyalkylates which contain sulfosuccinate groups and are based on resin acid esters of polyalcohols are known as dispersing agents for the fine dispersion and stabilization of solids and as wetting, emulsifying and leveling agents and dyeing auxiliaries from U.S. Pat. Nos. 4,297,270 and 4,312,631.

Aqueous pigment dispersions which are stable to flocculation and are prepared with the aid of block polymers of oxyalkylated aliphatic, aromatic or cycloaliphatic diamines are described in U.S. Pat. Nos. 3,841,888 and 3,947,287.

Dyeing auxiliaries which are used for dyeing wool with anionic dyestuffs and are obtained by half-esterification of oxyalkylated fatty amines with, maleic or phthalic anhydride are described in U.S. Pat. No. 4,778,919.

Block polymers of ethylenediamine derivatives using an alkylene oxide as an auxiliary are furthermore described for padding disperse dyestuffs onto hydrophobic synthetic fibers in the Japanese Patent Publication Sho-59-071 486. Block polymers of oxyalkylated alkylenediamines which are modified with styrene and partly sulfated with sulfuric acid are finally also known for use as leveling agents in the dyeing of synthetic material's from the Japanese Patent Publication Sho-58-191,283.

However, none of the products described in the abovementioned publications is suitable for decidedly improving the flow properties of printing inks without having an adverse influence on other parameters such as depth of color, gloss, color shade and dispersibility.

The present invention is based on the object of providing surface-active agents which are suitable for the production of solids dispersions having good flow properties, preferably coloring agent preparations for offset printing, and are largely free from the abovementioned disadvantages.

Esterification of oxyalkylates based on modified or nonmodified naturally occurring resin acids or resin amines or resin alcohols derived therefrom with dicarboxylic acids or anhydrides thereof and subsequent reaction with alkylenediamines or alkylenepolyamines gives pale yellowish, low-foaming surface-active substances which are surprisingly suitable for the production of solids dispersions having good flow properties, in particular coloring agent preparations having good flow properties.

The present invention thus relates to mixtures essentially comprising compounds of the formula (I)

$$A[(B)_m-Y-Z]_q \qquad (I)$$

in which

A is the radical of a modified or nonmodified naturally occurring resin acid or a resin amine or resin alcohol derived therefrom, or is the radical of an esterification product of 1 to 6, preferably 1 to 2, units of the resin acids mentioned with a polyhydric alcohol or of an esterification product of 1 to 12, preferably 1 to 6, units of the resin acids mentioned with an aminooxyalkylate of 1 to 5, preferably 1 to 3, units of the compound according to the formula (II)

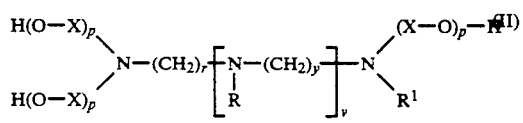

the esterification product still containing at least one free hydroxyl group, in which X is a group of the formula —CH$_2$CH$_2$—, —CH$_2$CH(CH$_3$)— or —CH(CH$_3$)CH$_2$— or is a combination thereof;

R is a hydrogen atom or the group —(X—O)$_p$—H,

R$^1$ is the group —(X—O)$_p$—H or the group —(X—O)$_p$—R$^2$, in which R$^2$ is a divalent group —OC—E—CO— which links two units of the compound of the formula (II) in ester form via the two free valencies shown and in which E is a divalent aromatic radical having 6 to 12 carbon atoms or a straight-chain, branched or cycloaliphatic alkylene group having 1 to 16 carbon atoms, preferably a straight-chain or branched alkylene group having 1 to 8 carbon atoms, v is an integer from zero to 4, preferably from zero to 2, and r and y are identical or different and are each an integer from 1 to 5;

p is an integer from 1 to 100, preferably from 1 to 20,

B is a direct bond, if A is an esterification product of at least one of the abovementioned resin compounds having at least one radical of a compound of the formula (II), or is a group of the formula —(X—O)—, in which X has the abovementioned meaning, Y is a group of the formula —OC—F—CO— or —OC—F—COO$^-$, in which F is a divalent aromatic radical having 6 to 12 carbon atoms or is a straight-chain, branched or cycloaliphatic alkylene group having in each case 1 to 16 carbon atoms, preferably straight-chain or branched C$_1$-C$_8$-alkylene, and Z is a group of the formula (IIIa)

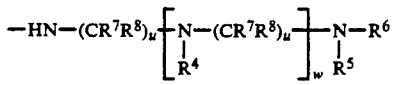

if Y is —OC—F—CO—, or is a cation of the formula (IIIb)

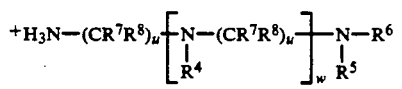

if Y is —OC—F—COO$^-$, in which $R^4$, $R^5$ and $R^5$ independently of one another are a hydrogen atom or a hydroxyalkylene having 1 to 6 carbon atoms, preferably having 2 or 3 carbon atoms, $R^7$ and $R^8$ independently of one another are hydrogen or methyl, u is identical or different and is an integer from 1 to 14, preferably from 2 to 3, and w is an integer from zero to 25, preferably from zero to 5, and m is a number from 1 to 100, preferably 5 to 30, and q is an integer from 1 to 11, preferably 1 to 6.

"Radical" is in each case understood as meaning the parent compound minus at least one hydrogen atom.

Compounds which are of particular interest are those of the formula (I) in which A is a radical of a naturally occurring resin acid, of a hydrogenated or disproportionated resin acid or of a resin amine or resin alcohol derived therefrom, or the radical of an esterification product which is obtained by esterification of 1 to 6, preferably 1 to 2, units of the above resin acids with a 2- to 6-hydric alcohol or of 1 to 12, preferably 1 to 6, units of the above resin acids with an aminooxyalkylate comprising 1 to 5, preferably 1 to 3, units of the formula (II), at least one free hydroxyl group being retained.

Compounds which are of particular interest are furthermore those of the formula (I) in which B is a direct bond if A is an esterification product prepared from at least one of the abovementioned resin compounds with an aminooxyalkylate of at least 1 to 5, preferably 1 to 3, units of the compound according to formula (II).

Compounds which are of particular interest are moreover those of the formula (I) in which B is the group of the formula —(X—O)—, in which X is a group of the formulae —CH$_2$CH$_2$—, —CH$_2$CH(CH$_3$)— and —CH(CH$_3$)—CH$_2$— or is a combination thereof.

Compounds which are of particular interest are additionally those of the formula (I) in which Y is a group of the formula —OC—F—CO— or —OC—F—COO$^-$, in which F is preferably a straight-chain or branched alkylene group having in each case 1 to 8 carbon atoms, in particular 1 to 4 carbon atoms, or is a divalent aromatic radical having 6 to 8 carbon atoms.

Compounds which are of interest are also those of the formula (I) in which Z is a group of the formula (IIIa) or (IIIb), in which $R^4$ and $R^5$ are each a hydrogen atom, $R^6$ is a hydrogen atom or a hydroxyalkylene having 2 or 3 carbon atoms and u and w have the abovementioned meanings.

Compounds which are of particular interest are likewise those of the formula (I) in which Z is a group of the formula (IIIa) or (IIIb), in which $R^4$, $R^5$ and $R^6$ are each a hydrogen atom, u is identical or different and is the number 2 or 3 and w is an integer from zero to 5.

The invention also relates to a process for the preparation of the compounds according to the invention. They are obtained by a1) oxyalkylating naturally occurring resin acids, resin alcohols or resin amines derived therefrom, disproportionated or hydrogenated resin acids or esterification products of the resin acids mentioned with polyhydric alcohols, the esterification products still containing at least one free hydroxyl group, with ethylene oxide or propylene oxide or both epoxides in succession or a mixture of both epoxides, 1 to 100 mol of epoxide being employed per reactive hydrogen atom in the resin compound used, or a2) esterifying the resin acids mentioned with aminooxalkylates of the formula (II), b) half-esterifying the products obtained in a1) or a2) on the terminal hydroxyl groups with dicarboxylic acids or dicarboxylic acid anhydrides c) and subsequently converting the free carboxyl groups of the carboxylic acid compound A[(B-)$_m$—CO—F—COOH]$_q$ chiefly formed with at least one diamine or polyamine on which the formula Z is based into the particular amide form or salt form.

Because of the large number of reaction centers in the starting compounds, no pure, uniform end product but a mixture, which nevertheless contains compounds according to the formula (I) as the main component, i.e. to the extent of more than 50% by weight, preferably to the extent of more than 90% by weight, is obtained in the preparation of the compounds according to the invention.

The degree of conversion in reaction stages a) and b) described above is characterized in th preparation examples by the hydroxyl number and the acid number, and the degree of conversion to the end product is characterized by the amine number.

The molecular weight of the compounds according to the invention can vary within a wide range and extends from 800 to 50000, preferably 1000 to 10000, in particular 1000 to 3000.

The following resin compounds on which the radical A is based are suitable, for example, for the preparation of the compounds according to the invention:

a) naturally occurring resin acids and their hydrogenation or disproportionation products, the resin compounds mentioned preferably being in the form of the commercially available colophony types or obtained therefrom;

b) resin amines such as are obtained from the resin acids mentioned under a) by conversion to the resin acid nitrile and subsequent hydrogenation;

c) resin alcohols such as are formed from the resin acids mentioned under a) by reduction, in particular hydrogenation;

d) esterification products such as are obtained by esterification of a nonmodified or a modified naturally occurring resin acid, such as are mentioned under a), with a 2- to 6-hydric alcohol or an aminooxyalkylate of the formula (II), it being necessary for 1 to 11, preferably 2 to 6, free hydroxyl groups still to be present in the esterification product.

Suitable starting substances are, preferably, naturally occurring resin acids, such as abietic acid, dehydroabietic acid, dihydroabietic acid, tetrahydroabietic acid, levopimaric acid, dextropimaric acid and isodextropimaric acid, such as exist in commercially available colophony types. Other substances which are furthermore preferably suitable are disproportionated, hydrogenated and dimerized resin acids, resin alcohols, such as abietyl alcohol and hydroabietyl alcohol, the commercially available mixture of dehydroabietyl, dihydroabietyl and tetrahydroabietyl alcohol (industrial hydroabietyl alcohol) also being suitable, and resin amines which are derived from the abovementioned resin acids, in particular dehydroabietylamine.

The following polyhydric alcohols, for example, are suitable for esterification of the resin acids in the production of the resin compounds mentioned under d): 1,2-ethanediol, 1,2-propanediol, 1,2- and 1,4-butanediol, 1,2,4-butanetriol, 1,1,1-trimethylolpropane, glycerol, polyglycerol, pentaerythritol, dipentaerythritol, trimethylolethane, neopentylglycol, 2,4-dihydroxy-3-methylolpentane, 1,2,6-hexanetriol, sorbitol, anhydrosorbitol, hexitol and mannitol, preferably glycerol and polyglycerol.

The aminooxyalkylates of the formula (II) are likewise suitable for esterification of the resin acids in the preparation of the resin compounds mentioned under d). Aminooxyalkylates of the formula (II) are described in K. Lindner, Tenside, Textilhilfsmittel, Waschrohstoffe (Surfactants, Textile Auxiliaries, Detergent Bases), Springer-Verlag, 1964, pages 1055 to 1056. The aminooxyalkylates of the formula (II) can be prepared by customary methods by oxyalkylating the corresponding diamine or polyamine with ethylene oxide, propylene oxide or a mixture thereof at a temperature of 80° to 160° C., preferably 110° to 140° C., under a pressure of 2 to 8 bar, preferably 3 to 5 bar, advantageously with addition of alkaline catalysts. Two or more aminooxyalkylate units of the formula (II) can be linked by esterification of an aminooxyalkylate with at least one dicarboxylic acid or dicarboxylic acid anhydride in a molar ratio of aminooxyalkylate to dicarboxylic acid (anhydride) of 2:1 to 5:4, preferably 2:1 to 3:2, in at least one reaction stage.

Suitable dicarboxylic acids for the production of the compounds according to the invention are, preferably, aliphatic dicarboxylic acids having 3 to 12 carbon atoms, in particular malonic acid, succinic acid, glutaric acid, adipic acid, 1,5-pentanedicarboxylic acid, 1,6-hexanedicarboxylic acid and 1,10-decanedicarboxylic acid, and also, for example, cyclohexane-1,4-dicarboxylic acid as well as phthalic acid and terephthalic acid. Suitable anhydrides are, in particular, maleic anhydride, succinic anhydride, glutaric anhydride and phthalic anhydride.

The aminooxyalkylates can be linked with the dicarboxylic acids mentioned or anhydrides thereof by esterification methods which are customary per se. The reaction temperature here is between 0° C. and 240° C., preferably 130° to 180° C., depending on the esterification method. The esterification is preferably carried out in an inert organic solvent which is suitable as an entraining agent for removal of the water of reaction, in order to increase the yield. For example, the esterification can be carried out in xylene as the organic solvent and in the presence of acid catalysts at a temperature of 130° to 220° C., preferably 140° to 170° C., while the esterification with maleic anhydride, succinic anhydride or phthalic anhydride is carried out at 0° C. to 150° C., preferably at 40° to 80° C. in the case of maleic anhydride and preferably at 90° to 120° C. in the case of succinic anhydride and phthalic anhydride.

Suitable acid catalysts are organic and inorganic acids, for example benzenesulfonic acid, p-toluenesulfonic acid, boric acid and sulfuric acid, Lewis acids, such as zinc chloride or tin powder and mixtures thereof, or acid ion exchangers. It is advantageous to employ the organic and inorganic acids and the Lewis acids in a concentration of 0.05 to 3% by weight, preferably 0.5 to 1% by weight, to employ tin powder in a concentration of 2 to 5% by weight, preferably 3 to 4% by weight, and to employ the acid ion exchangers in a concentration of 3 to 10% by weight, preferably 5 to 7% by weight, in each case based on the oxyalkylate to be esterified.

The nonmodified or modified naturally occurring resin acids are esterified with a polyhydric alcohol or with an aminooxyalkylate of 1 to 5 units of the compound of the formula (II) in a molar ratio such that the particular esterification product still contains 1 to 11, preferably 2 to 6, free hydroxyl groups. A molar ratio of resin acid to polyhydric alcohol or aminooxyalkylate of 1:1 to 3:1 is preferably used. The esterification reaction can be carried out by customary processes at about 100° to 300° C., preferably at 160 to 270° C., if appropriate with addition of an entraining agent, for example an aromatic hydrocarbon or chlorohydrocarbon, if appropriate also with the addition of a catalyst, such as benzenesulfonic acid, p-toluenesulfonic acid, boric acid, sulfuric acid, hydrochloric acid and tin powder, in the abovementioned concentrations.

The oxyalkylation of the nonmodified or modified naturally occurring resin acids, resin alcohols, resin amines and resin acid esters from which the radical A in the general formula (I) is derived can be carried out by customary methods. Preferably, the particular resin substance is reacted with ethylene oxide or propylene oxide or both epoxides (in alternation or as a mixture) at a temperature of 100° to 200° C., preferably at 120° to 160° C., in the presence of a hydroxide or an alkoxylate as the catalyst, preferably an alkali metal hydroxide, such as potassium hydroxide or in particular sodium hydroxide, or an alkali metal alkoxylate, such as sodium methylate or sodium ethylate. The amount of the epoxides used or of the epoxide mixture is chosen so that 1 to 100 mol, preferably 2 to 20 mol, of the epoxide or epoxides used are added on per reactive hydrogen atom of the free carboxyl groups, hydroxyl groups and amino groups of the particular resin substance. The concentration of the alkali metal hydroxide or alkali metal alkoxylate catalyst should preferably be 0.05 to 1.0% by weight, based on the resin substance, at the start of the oxyalkylation. The oxyalkylation can be carried out under normal pressure or in pressure vessels with propylene oxide or, preferably, with ethylene oxide or with mixtures of both epoxides, it being possible for the alkylene oxide to be added in gaseous or liquid form. The operating pressure is as a rule 1 to 10 bar, preferably 2 to 8 bar. The amount of alkylene oxide added on can be varied and optimized according to the intended use and the required degree of hydrophilicity of the amine condensates or amine salts of the formula (I) produced from the oxyalkylation products.

The reaction of the amines on which the formula Z is based with the oxyalkylated resin substance prepared in the preceding reaction step is carried out after half-esterification of the terminal hydroxyl groups of the oxyalkylated resin substances with suitable dicarboxylic acids or anhydrides thereof. The following are suitable, for example, for the esterification: maleic acid, maleic anhydride, fumaric acid, phthalic acid, phthalic anhydride, isophthalic acid, terephthalic acid, oxalic acid, malonic acid, succinic acid, succinic anhydride, glutaric acid, glutaric anhydride, adipic acid, pimelic acid, suberic acid, azelaic acid and sebacic acid. The oxyalkylates are half-esterified with the dicarboxylic acids mentioned by customary processes at 130° to 220° C., preferably at 150° to 180° C., in the presence of inorganic or organic acids or of Lewis acids, such as zinc chloride, benzenesulfonic acid, p-toluenesulfonic acid, boric acid, tin powder or sulfuric acid, in the abovementioned concentrations. The water of reaction which forms is removed by distillation, if appropriate with addition of an entraining agent, for example a hydrocarbon or chlorohydrocarbon. If dicarboxylic acid anhydrides are used, the half-esterification is already carried out at 0° to 150° C., preferably at 40° to 120° C., if appropriate in the presence of alkali metal hydroxides, in which case the concentration of the alkali metal hydroxides should be 0.1 to 1.0% by weight, based on the total mixture. In the case of maleic anhydride, succinic anhydride and phthalic anhydride, it is advantageous, because of the tendency toward sublimation, to carry out the reaction in pressure vessels under an increased pressure of 0.2 to 1.0 bar of nitrogen or air and to ensure vigorous mixing, since the molten anhydrides are miscible with the oxyalkylated resin compounds to only a small extent at the start of the reaction.

The oxyalkylation products provided with a carboxyl group are then reacted with the amines on which Z is based to give either amides or amine salts, approximately the equimolar amount of the amine being employed per free carboxyl group of the particular half-ester. In the case of amidation, the reaction temperature to be observed is usually between 20° and 240° C., but is preferably 130° to 180° C., depending on the amidation method. The amidation is preferably carried out in an inert organic solvent which is a suitable entraining agent for removal of the water of reaction, in order to increase the yield. For example, the amidation can be carried out in xylene as the organic solvent and in the presence of acid catalysts at a temperature of 130° to 220° C. Suitable acid catalysts are, for example, acids and Lewis acids, such as benzenesulfonic acid, p-toluenesulfonic acid, boric acid, tin powder, zinc chloride or sulfuric acid.

In contrast, the amine salts are prepared at a temperature of 20° to 130° C., preferably at 40° to 90° C., in particular 70° to 90° C.

The yield of end product both in the amidation and in the preparation of the amine salt is more than 90% of the theoretical value.

Examples of the amines on which Z is based, Z being the formula (IIIa) or (IIIb) mentioned, are alkylenediamines and polyamines of the formula $H[-NH-(CR^7R^8)_u]_w-NH_2$, in which $R^7$, $R^8$, u and w have the meanings given for the formulae (IIIa) and (IIIb).

Such compounds are, for example, 1,2-diaminoethane, 1,3-diaminopropane, 1,2-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,12-diaminododecane, diethylenetriamine, dipropylenetriamine, triethylenetetramine, dipropylenetetramine, tetraethylenepentamine, tetrapropylenepentamine, pentaethylenehexamine, pentapropylenehexamine, hexaethyleneheptamine, hexapropyleneheptamine, heptaethyleneoctamine, heptapropyleneoctamine, 1,3-diamino-2,2-dimethyl-propane, 1,2-diamino-2-methyl-propane, 1,3-diamino-2-methyl-propane, 2,5-diamino-2,5-dimethylhexane, N-(2-aminoethyl)-1,3-propylenediamine and N,N'-bis(3-aminopropyl)ethylenediamine.

Amines which are furthermore suitable are those of the formula $H[-NH-(CH_2)_u-]_w-NH-CH_2CH_2OH$, in which u and w have the meanings given for the formulae (IIIa) and (IIIb), for example alkylolamines, such as N-(2-hydroxyethyl)-1,2-diaminoethane, N-(2-hydroxyethyl)diethylenetriamine, N-(2-hydroxyethyl)triethylenetetramine and 2-aminoethanol.

The invention also relates to the use of the compounds according to the invention as surface-active agents. Because of their diverse surface-active properties, the substances according to the invention have a broad use spectrum. They belong to the class of surface-active compounds according to DIN 53 900, reduce surface tension by the ring pull-off method (DIN 53 914) and are to be described as nonfoaming or low-foaming surface-active substances from the results in the modified Ross-Miles test (DIN 53 902). With a suitable degree of hydrophilicity, they exhibit an excellent wetting power for cotton by the dip-wetting method (DIN 53 901), coupled with good leveling properties according to DIN 53 504. Their use as wetting and leveling agents and dyeing auxiliaries is therefore advantageous. They furthermore have a very good flocculation-preventing power (DIN 53 908) against pigments and dyestuffs and can moreover be used as retention agents.

The substances according to the invention can be used either as emulsifiers or as dispersing agents for solids dispersions. This applies above all to use as coupling auxiliaries or preparation agents or both in the production of azo compounds, preferably azo coloring agents, in particular azo pigments for offset printing, as dispersing agents for the fine dispersion and stabilization of sparingly soluble or insoluble coloring agents and for the production of pigments dispersions having good flow properties.

The substances according to the invention are furthermore suitable as additives and emulsifiers for the production of fat and mineral oil emulsions, for example as corrosion protection additives, and as additives for the production of cooling lubricants and cold rolling oils in the metalworking industry.

The compounds according to the invention can be employed individually or as mixtures, as well as in combinations with other nonionic or cationic surfactants or mixtures thereof. They can furthermore be used together with customary amounts of matrix substances or other customary additives or auxiliaries in emulsifying and dispersing agent formulations.

In the following examples, "parts" and percentage data relate to the weight and parts by weight bear the same relationship to parts by volume as the kilogram to the liter. Pressure data are "increased pressure", relative to atmospheric pressure, unless stated otherwise. The acid number (AN) is determined in accordance with DIN 53 402. The acid number indicates the amount of potassium hydroxide in milligrams which is consumed for neutralization of 1 g of the reaction product.

The hydroxyl number is determined in accordance with DIN 53 240 and indicates the amount of potassium hydroxide in milligrams which is consumed to react 1 g of the reaction product. The amine number is determined in accordance with DIN 53 176 and is that amount of potassium hydroxide in milligrams which is equivalent to the amine content of 1 g of substance.

PREPARATION EXAMPLE 1 a) Preparation of the resin acid oxyethylate 302 parts of colophony were oxyalkylated, after addition of 2.2 parts of sodium methylate, while stirring and adding 440 parts of ethylene oxide in a pressure vessel at 150° to 160° C., a pressure of 4 to 6 bar being maintained. When all the ethylene oxide had been forced in, the mixture was subsequently stirred at 150° to 160° C. for one hour. The resin acid adduct thus obtained is brown and viscous and contains on average 10 ethyleneoxy units per molecule at a hydroxyl number according to DIN 53 240 of 75.0.

b) Preparation of the malonic acid ester 300 parts of resin acid oxyethylate a) were heated to 70 to 80° C. with 42.0 parts of malonic acid and the mixture was stirred for one hour under nitrogen gas. After addition of 1.5 parts of p-toluenesulfonic acid and 150 parts of xylene, the mixture was heated at 150° to 160° C. for 16 hours, the water of reaction being removed from the circulation using a water separator. The xylene was then distilled off and the acid number was determined in accordance with DIN 53 402. The product has an acid number of 72.3.

c) Preparation of the resin amine condensate 300 parts of malonic acid ester b) were initially introduced into the reaction vessel and were mixed thoroughly with 40.2 parts of N-(2-hydroxyethyl)-1,2-diaminoethane, corresponding to the acid number, at 60° to 70° C. After addition of 0.5 part of p-toluenesulfonic acid and 150 parts of xylene, amidation was carried out analogously to the esterification b) to an acid number of less than 20. A dark brown, waxy-soft product having an amine number of between 115 and 120 was obtained.

PREPARATION EXAMPLE 2 a) Preparation of the resin alcohol oxyethylate 292 parts of industrial hydroabietyl alcohol (Hercules, USA) were oxyalkylated, after addition of 1 part of potassium hydroxide, while stirring and passing in 528 parts of ethylene oxide in a pressure vessel at 150° to 160° C., a pressure of about 1.5 to 2 bar being maintained. When all the ethylene oxide had been forced in, the mixture was subsequently stirred at 150° to 160° C. for one hour. The resulting resin alcohol adduct contains on average 12 ethyleneoxy units per molecule and has a
hydroxyl number of between 65 and 70.

b) Preparation of the succinic acid half-ester 300 parts of resin alcohol oxyethylate a) were heated to 50° to 60° C. and 36.76 parts of succinic anhydride were introduced in portions. After the reaction temperature had been increased to 100° to 120° C., the mixture was subsequently stirred for 3 to 4 hours, while covering with a layer of nitrogen. The resulting succinic acid half-ester contains on average one carboxyl group per molecule and has an average acid number of 63.

c) Preparation of a diethylenetriamine salt 300 parts of succinic acid half-ester b) were converted into the amine salt at initially 60° to 70° C. by addition of a solution of 34.7 parts of diethylenetriamine and 502.1 parts of demineralized water in the course of 1 to 2 hours with the reaction temperature falling to 20° to 25° C. The amount of water added can amount to between 50 and 85% of the end product. The aqueous amine salt has an amine number of about 164, based on the solid, and a pH of 8.6.

PREPARATION EXAMPLE 3 a) Preparation of the resin acid monoglycerol ester 302 parts of colophony were esterified to an acid number (DIN 53 402) of 20 with 92 parts of glycerol in the presence of 4 parts of tin powder in a suitable stirred vessel at 230° to 250° C. in the course of 8 to 10 hours, the water of reaction being distilled off and nitrogen simultaneously being passed through.

b) Preparation of the resin acid glycerol ester oxyethylate 356 parts of resin acid monoglycerol ester according to a) were oxyalkylated, after addition of 2.7 parts of sodium methylate (30% strength in methanol), while stirring and adding 440 parts of ethylene oxide in a pressure vessel at 150° to 160° C., a pressure of 2 to 8 bar being maintained. When all the ethylene oxide had been forced in, the mixture was stirred at 150° to 160° C. for a further hour. The resulting resin acid glycerol ester oxyethylate contains on average 10 ethyleneoxy units per molecule and has a hydroxyl number of between 135 and 140.

c) Preparation of the di-maleic acid half-ester 300 parts of resin acid glycerol ester oxyethylate b) were esterified to an acid number of between 108 and 112 with 72.0 parts of maleic anhydride at 75° to 80° C. in the course of 3 to 4 hours analogously to Preparation Example 2b).

d) Preparation of the resin amine condensate 300 parts of di-maleic acid half-ester c) were amidated with 61.4 parts of N-(2-hydroxyethylene)-1,2-diaminoethane, corresponding to the acid number, using 1.5 parts of p-toluenesulfonic acid in 150 parts of xylene at 155° to 165° C. in the course of about 10 hours, analogously to Preparation Example 1c). A brown, waxy-soft product having an amine number of between 185 and 195 was obtained.

PREPARATION EXAMPLE 4 a) Preparation of the resin acid oxyethylate 302 parts of colophony were reacted with 1320 parts of ethylene oxide, after addition of 0.5 part of pulverulent caustic soda, in accordance with Preparation Example 1a). The product contains on average 30 ethyleneoxy units per molecule and has a hydroxyl number of between 30 and 35.

b) Preparation of the phthalic acid half-ester 500 parts of resin acid oxyethylate a) were heated about 50° C., 43.0 parts of phthalic acid, corresponding to the hydroxyl number which exists, were introduced in portions and the mixture was stirred at 100° to 120° C. under nitrogen for 3 to 4 hours. A yellow-brown, viscous phthalic acid half-ester having an acid number of 32 was obtained.

c) Preparation of a triethylenetetramine salt 300 parts of phthalic acid half-ester were heated to 50° to 60° C. and converted into the amine salt, in accordance with the acid number, in the course of about 1 hour by introducing 25 parts of triethylenetetramine and increasing the reaction temperature to 65° to 75° C. A yellow-brown amine product having an amine number of between 90 and 100 was obtained.

PREPARATION EXAMPLE 5 a) Preparation of the resin amine oxyethylate 4.5 parts of sodium methylate (30% strength in methanol) were added to 286 parts of industrial dehydroabietylamine (Amine D from Hercules, USA) in a pressure vessel and, after the excess methanol had been removed, the mixture was reacted by feeding in 440 parts of ethylene oxide at 120° to 140° C. while maintaining a pressure of between 1.5 and 2.5 bar. When all the amount of ethylene oxide had been forced in, the mixture was stirred at 130° to 140° C. for a further hour. A viscous brown product having on average 10 ethylene oxide units per molecule and a hydroxyl number of 155 was obtained.

b) Preparation of the di-maleic acid half-ester 300 parts of resin amine oxyethylate a) were reacted with 81.2 parts of maleic anhydride at 75° to 80° C. in the course of 3 to 4 hours analogously to Preparation Example 2b). A yellow, waxy-soft di-maleic acid half-ester having an acid number of about 122 was obtained.

c) Preparation of the resin amine condensate 300 parts of di-maleic acid half-ester b) were amidated in accordance with the acid number, after addition of 1.5 parts of p-toluenesulfonic acid and 150 parts of xylene, with 136 parts of N-(2-hydroxyethyl)-1,2-diaminoethane at 155° to 165° C. according to Preparation Example 1c). A brown, waxy-soft amine condensate having an amine number of about 200 was obtained.

PREPARATION EXAMPLE 6 a) Preparation of the resin acid monopentaerythritol ester 302 parts of colophony were esterified to an acid number of 15 with 136 parts of pentaerythritol in the presence of 4.5 parts of boric acid in accordance with Preparation Example 3a).

b) Preparation of the resin acid monopentaerythritol ester oxyethylate 420 parts of resin acid monopentaerythritol ester a) were reacted, after addition of 3.1 parts of sodium methylate (30% strength in methanol) with 660 parts of ethylene oxide in accordance with Preparation Example 3b). The resulting resin acid monopentaerythritol ester oxyethylate contains on average 15 ethyleneoxy units per molecule and has a hydroxyl number of 153.

c) Preparation of the tri-maleic acid half-ester 300 parts of resin acid monopentaerythritol ester oxyethylate b) having a hydroxyl number of 153 were esterified with 80 parts of maleic anhydride at 75° to 80° C. in the course of 4 hours in accordance with Preparation Example 2b). A yellow, waxy esterification product having an acid number of between 120 and 125 was obtained.

d) Preparation of a tri-1,2-ethylenediamine salt 300 parts of tri-maleic acid half-ester c) were reacted by addition of 39 parts of 1,2-ethylenediamine (calculated with respect to the acid number) in portions at 60° to 70° C. in the course of 1 to 1.5 hours. A yellow-brown, waxy product having an amine number of between 195 and 210 was obtained.

PREPARATION EXAMPLE 7 a) Preparation of the resin amine oxyethylate 286 parts of industrial dehydroabietylamine (Amine D from Hercules, USA) were initially introduced into the reaction vessel and reacted with 232 parts of propylene oxide at 120° to 140° C. under a pressure of 3 to 4 bar. After a subsequent stirring time of 1 hour and after addition of 6 parts of sodium methylate (30% strength in methanol) and removal of the methanol, 264 parts of ethylene oxide were fed in at the same temperature and under the same pressure conditions and the mixture was subsequently stirred again at 140° to 145° C. under a pressure of 3 to 4 bar for 1 hour. A viscous yellow-brown resin amine oxyalkylate which contains on average 4 propylene oxide units and 6 ethylene oxide units per molecule was obtained. The hydroxyl number of the oxyalkylate is between 140 and 150.

b) Preparation of the di-maleic acid half-ester 300 parts of resin amine oxyalkylate a) were esterified, according to the hydroxyl number of 143.5, with 75.2 parts of maleic anhydride at 75° to 80° C. in the course of 3 to 4 hours, analogously to Preparation Example 2b). A yellow half-ester product having an acid number of 115 was obtained.

c) Preparation of a diethylenetriamine salt 300 parts of di-maleic acid half-ester b) were reacted with 63.9 parts of diethylenetriamine in the course of 1 to 1.5 hours in accordance with Preparation Example 6d). The resulting amine product has a pH of between 8.9 and 9.3 and an amine number of about 286.

PREPARATION EXAMPLE 8 a) Preparation of the diaminopropane oxyalkylate 50 parts of 1,3-diaminopropane were reacted at 90° to 110° C., while stirring and adding 162 parts of propylene oxide, and after addition of 3 parts of sodium methylate (30% strength in methanol) and removal of the methanol under reduced pressure, the product was oxyethylated with 982.8 parts of ethylene oxide at 120° to 140° C. under 3 to 5 bar. The resulting oxyalkylate contains 4 propylene oxide units and 20 ethylene oxide units per molecule. The oxyalkylate present has a hydroxyl number of 191.5.

b) Preparation of the di-resin acid ester 300 parts of 1,3-diaminopropane oxyalkylate a) were esterified with 155 parts of disproportionated colophony in the presence of 6 parts of tin powder and 1.5 parts of p-toluenesulfonic acid at 155° to 165° C. in the course of 10 hours in accordance with Preparation Example 3a). The resulting brown, viscous resin ester has a hydroxyl number of 64.4.

c) Preparation of the di-maleic acid half-ester 400 parts of di-resin acid ester b) were esterified, in accordance with the hydroxyl number, to an acid number of 57 with 44.9 parts of maleic anhydride at 75° to 80° C. in the course of 3 to 4 hours, analogously to Preparation Example 3a).

d) Preparation of a diethylenetriamine salt 300 parts of di-maleic acid half-ester c) were reacted, in accordance with the acid number, with a solution of 31.7 parts of diethylenetriamine and 487.5 parts of demineralized water in the course of 1 to 1.5 hours in accordance with Preparation Example 2c). The amount of water added can amount to between 50 and 85% of the end product. The amine salt present has a pH of 8.2 and an amine number of about 210.

PREPARATION EXAMPLE 9 a) Preparation of the 1,2-diaminoethane oxyalkylate 50 parts of 1,2-diaminoethane were oxypropylated at 90° to 110° C., while stirring and adding 195 parts of propylene oxide, and after addition of 3 parts of sodium ethylate (30% strength in methanol) and removal of the methanol under reduced pressure, the product was reacted with 880 parts of ethylene oxide at 120° to 140° C. under 3 to 5 bar. The resulting oxyalkylate contains 4 propylene oxide units and 24 ethylene oxide units per molecule and has a hydroxyl number of about 163.

b) Preparation of an aminooxyalkylate with 3 linkages 600 parts of 1,2-diaminoethane oxyalkylate a) were heated, in accordance with the hydroxyl number of 163 and after addition of 3 parts of p-toluenesulfonic acid and 200 parts of xylene as an entraining agent, with 30.9 parts of malonic acid at 155° to 165° C. for 10 hours and the water of reaction was removed from the circulation. After the xylene had been distilled off, the product had an acid number of less than 10, a hydroxyl number of about 106 and a content of 12 propylene oxide and 72 ethylene oxide units per molecule.

c) Preparation of a 4-fold resin ester 400 parts of the aminooxyalkylate b) with 3 linkages were esterified, in accordance with a hydroxyl number of 53, to an acid number of about 10 with 114 parts of disproportionated colophony in accordance with Preparation Example 3a).

d) Preparation of a 4-fold maleic acid half-ester 200 parts of resin acid aminooxyalkylate ester c) were half-esterified, in accordance with the hydroxyl number of 26 still present, with 18.5 parts of maleic anhydride at 75° to 85° C. in the course of 3 to 4 hours and the product was then reacted, in accordance with an acid number of 76.6, with a solution of 31 parts of diethylenetriamine and 374.3 parts of water at a temperature falling from 60° C. down to 20° to 25° C. in the course of 1 to 1.5 hours. A yellow-brown amine salt solution having a pH of about 8.5 and an amine number of about 200 was obtained. The amount of water added preferably amounted to between 50 and 80% of the finished solution of the product.

PREPARATION EXAMPLE 10 a) Preparation of the diethylenetriamine oxyalkylate 50 parts of diethylenetriamine were reacted with 281.3 parts of propylene oxide and, after addition of 2.5 parts of sodium methylate (30% strength in methanol) and removal of the methanol under reduced pressure, the product was reacted with 853.3 parts of ethylene oxide, analogously to Preparation Example 8a). The pale yellow oxyalkylate contained 10 propylene oxide units and 40 ethylene oxide units per molecule, at a hydroxyl number of about 115.

b) Preparation of the 2-fold resin ester 300 parts of diethylenetriamine oxyalkylate a) were esterified to an acid number of less than 10 with 73.6 parts of disproportionated colophony, analogously to Preparation Example 3a). The hydroxyl number of the product is 55.

c) Preparation of the tri-maleic acid half-ester 300 parts of the 2-fold resin ester b) were esterified, in accordance with the hydroxyl number, with 29.2 parts of maleic anhydride at 75° to 80° C. in the course of 3 to 4 hours in accordance with Preparation Example 3c). The resulting brown, viscous half-ester has an acid number of about 170.

d) Preparation of a 1,2-ethanediamine salt 400 parts of tri-maleic acid half-ester c) were reacted, in accordance with the acid number, with a solution of 72.7 parts of 1,2-ethanediamine in 709 parts of demineralized water, analogously to Preparation Example 8d). The amount of water added can amount to between 50 and 85% of the finished solution of the product. The aqueous amine salt has an amine number of about 143 and a pH of 8.8.

PREPARATION EXAMPLE 11

Preparation of a resin amine condensate 500 parts of resin amine oxyalkylate corresponding to Preparation Example 8a) were esterified to an acid number of 118, in accordance with the hydroxyl number of 143.5, with 125.3 parts of maleic anhydride at 75° to 80° C. in the course of 3.5 to 4 hours. 136.8 parts of N-(2-hydroxyethyl)-1,2-diaminoethane, calculated with respect to the acid number, were then mixed in and stirred thoroughly at the same temperature in the course of 30 to 60 minutes. After 1.5 parts of p-toluenesulfonic acid and 200 ml of xylene had been added and the reaction temperature had been increased to 155 to 165° C., the water of reaction was removed from the circulation in the course of 8 to 12 hours. Thereafter, the xylene was distilled off in vacuo. A dark brown, waxy-soft product having an acid number of less than 25 and an amine number of 238 was obtained.

USE EXAMPLE 1

60.2 parts of 1-acetoacetylamino-2,4-dimethylbenzene and 6.1 parts of 1-acetoacetylamino-2,5-dimethoxy-4-chlorobenzene were dissolved in 900 parts of water and 31 parts by volume of 33% strength sodium hydroxide solution and, after addition of 1.5 parts of a fatty alcohol polyglycol ether, a precipitate was obtained with the aid of 22 parts by volume of acetic acid. After addition of 2.5 parts of the product from Preparation Example 7, the precipitate was coupled with a solution of tetrazotized 4,4'-diamino-3,3'-dichlorodiphenyl, the tetrazonium salt solution being prepared by addition of 60 parts by volume of aqueous 5 normal sodium nitrite solution to a mixture of 38 parts by volume of 4,4'-diamino-3,3'-dichlorodiphenyl, 183 parts by volume of 5 normal hydrochloric acid and 520 parts of water. When the coupling had ended, 2.5 parts of dehydroabietylamine were added to the pigment suspension, the suspension was rendered alkaline, a solution containing 1.8 parts of dimethyl-coconut fatty amine oxide and 36 parts of a partly hydrogenated colophony was then added and the mixture was heated at 98° C. for 30 minutes. Thereafter, the pH was brought to 4 with hydrochloric acid and the mixture was heated at 98° C. for a further 30 minutes. It was then filtered and the product was washed and dried. A pigment preparation which resulted in a printing ink having very good use properties when incorporated into a printing ink varnish for letterpress and offset printing was obtained. Compared with a printing ink which had been prepared without addition of the product from Preparation Example 7, the printing ink is distinguished by improved flow properties.

USE EXAMPLE 2

The product from Preparation Example 7 used in Use Example 1 was replaced by the product from Preparation Example 8. A pigment preparation having similarly good properties to those described in Use Example 1 was obtained.

USE EXAMPLE 3

The product from Preparation Example 7 used in Use Example 1 was replaced by the product from Preparation Example 3. A pigment preparation having similarly good properties to those described in Use Example 1 was obtained.

USE EXAMPLE 4

The product from Preparation Example 7 used in Use Example 1 was replaced by the product from Preparation Example 11. A pigment preparation having similarly good properties to those described in Use Example 1 was obtained.

USE EXAMPLE 5

32.3 parts of 1-acetoacetylamino-2,4-dimethylbenzene and 30.1 parts of 1-acetoacetylamino-2-methylbenzene were dissolved in 750 parts of water and 31 parts by volume of 33% strength sodium hydroxide solution and, after addition of 1.5 parts of a fatty alcohol polyglycol ether, a precipitate was obtained with 22 parts by volume of acetic acid. After addition of 2.5 parts of the product from Preparation Example 7, the precipitate was coupled with a solution of 38 parts of tetrazotized 4,4'-diamino-3,3'-dichlorodiphenyl, which is prepared analogously to Use Example 1.

The pigment suspension was then rendered alkaline, a solution of 28 parts of a balsam resin was added and the mixture was heated at 98° C. for 1 hour. The pH was then brought to 4 with hydrochloric acid and the mixture was heated at 98° C. for a further hour. It was then filtered and the product was washed and dried. A printing ink produced analogously to Use Examples 1 to 4 has comparably good printing properties, in particular improved flow properties in comparison with a printing ink which had been produced without addition of the compound from Preparation Example 7.

USE EXAMPLE 6

The product from Preparation Example 7 used in Use Example 5 was replaced by the product from Preparation Example 11. A pigment preparation having similarly good properties to those described in Use Example 5 was obtained.

USE EXAMPLE 7

520 parts of Pigment Red 12 (Colour Index Number 12370) were kneaded into a viscous form with 72 parts of the diethylenetriamine salt according to Preparation Example 8, 35 parts of 1,2-propanediol and 140 parts of water in a twin-bowl kneader for about one hour. After the pigment had become finely dispersed, the mixture was diluted by addition of a further 125 parts of 1,2-propanediol and 109 parts of water. The 52% strength pigment preparation has good flow properties and is outstandingly suitable for coloring aqueous paints and for use in the dyeing of paper pulp.

USE EXAMPLE 8

400 parts of Pigment Yellow 16 (Colour Index Number 20040) were ground with 52 parts of the diethylenetriamine salt according to Preparation Example 8, 200 parts of 1,2-propanediol and 110 parts of water in a stirred bead mill with 1 mm ailiquarzite glass beads until the required fine dispersion is achieved. 238 parts of water were then added to the ground material and the thinly liquid pigment dispersion was separated from the grinding bodies via a sieve. The 40% strength by weight pigment dispersion could be further diluted with water in any proportion and is particularly suitable for coloring aqueous or alcohol-containing flexographic and/or gravure printing inks.

USE EXAMPLE 9

A pigment dispersion having similarly good properties was obtained by replacing the 171 parts of the diethylenetriamine salt according to Preparation Example 8 by 52 parts of the 4-fold maleic acid half-ester according to Preparation Example 9.

USE EXAMPLE 10

75 parts of methylnaphthalene were stirred homogeneously with 25 parts of diethylenetriamine salt according to Preparation Example 7. The concentrate was then made up to 1000 parts by volume with water. A finely disperse carrier emulsion which has an outstanding stability at the dilution usually used (1:10) and can be used for a relatively long period of time was obtained.

USE EXAMPLE 11

70 parts of an aromatic-containing mineral oil were stirred homogeneously with 20 parts of the diethylenetriamine salt according to Preparation Example 8 and 10 parts of the resin amine condensate according to Preparation Example 11 and the mixture was then diluted to 900 parts by volume with water. A finely disperse to transparent mineral oil emulsion which, after a dilution of 1:9, additionally has corrosion protection properties according to DIN 51 360, as well as an outstanding stability over a relatively long period of time, was obtained.

We claim:

1. A compound of the formula (I)

$$A[(B)_m-Y-Z]_q \qquad (I)$$

in which
A is the radical of a modified or nonmodified naturally occurring resin acid or a modified or non-modified resin amine or a modified or non-modified resin alcohol or is the radical of an esterification product of 1 to 6 units of the resin acids mentioned with a polyhydric alcohol or of an esterification product of 1 to 12 units of the resin acids mentioned with an aminooxyalkylate of 1 to 5 units of the compound according to the formula (II)

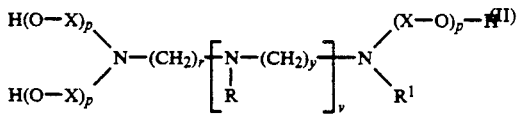

the esterification product still containing at least one free hydroxyl group,
in which
X is a group of the formula —CH$_2$CH$_2$—, —CH$_2$CH(CH$_3$)— or —CH(CH$_3$)CH$_2$— or is a combination thereof;
R is a hydrogen atom or the group —(X—O)$_p$—H,
R$^1$ is the group —(X—O—)$_p$—H or the group —(X—O—)$_p$—R$^2$, in which R$^2$ is a divalent group —OC—E—CO— which links two units of the compound of the formula (II) in ester form via the two free valencies shown and in which E is a divalent aromatic radical having 6 to 12 carbon atoms or a straight-chain, branched or cycloaliphatic alkylene group having 1 to 16 carbon atoms, v is an integer from zero to 4 and r and y are identical or different and are each an integer from 1 to 5;
p is an integer from 1 to 100,
B is a direct bond, if A is an esterification product of at least one of the abovementioned resin compounds having at least one radical of a compound of the formula (II), or is a group of the formula —(X—O)—, in which X has the abovementioned meaning,
is a group of the formula —OC—F—CO— or —OC—F—COO$^-$, in which F is a divalent aromatic radical having 6 to 12 carbon atoms or is a straight-chain, branched or cycloaliphatic alkylene group having in each case 1 to 16 carbon atoms and
Z is a group of the formula (IIIa)

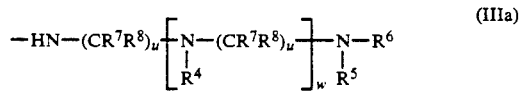

if Y is —OC—F—CO—, or is a cation of the formula (IIIb)

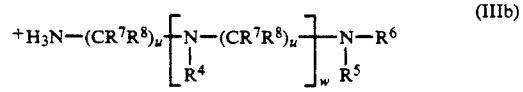

if Y is —OC—F—COO$^-$,
in which R$^4$, R$^5$ and R$^6$ independently of one another are a hydrogen atom or a hydroxyalkylene having 1 to 6 carbon atoms, R$^7$ and R$^8$ independently of one another are hydrogen or methyl, u is identical or different and is an integer from 1 to 14, and w is an integer from zero to 25, and
m is a number from 1 to 100 and
q is an integer from 1 to 11.

2. A compound as claimed in claim 1, wherein, in the group Z of the formula (IIIa) or (IIIb)
R$^4$ and R$^5$ are each a hydrogen atom and R$^6$ is a hydrogen atom or a hydroxyalkylene having 2 or 3 carbon atoms.

3. A compound as claimed in claim 1, wherein, in the group Z of the formula (IIIa) or (IIIb),
R$^4$, R$^5$ and R$^6$ are each hydrogen,
u is identical or different and is the number 2 or 3 and w is an integer from zero to 5.

4. A compound as claimed in claim 1, wherein Y is a group of the formula —OC—F—CO— or —OC—F—COO—, in which F is a divalent aromatic radical having 6 to 8 carbon atoms or is a straight-chain or branched alkylene group having 1 to 8 carbon atoms.

5. A compound as claimed in claim 4, wherein F is a straight-chain or branched alkylene group having to 4 carbon atoms.

6. A compound as claimed in claim 1, wherein
B is a group of the formula —(X—O—)—, in which
X is a group of the formula —CH$_2$CH$_2$—, —CH$_2$CH(CH$_3$)— or —CH(CH$_3$)—CH$_2$— or is a combination thereof.

7. A compound as claimed in claim 1, wherein
B is a direct bond if A is an esterification product prepared from at least one of the resin compounds mentioned in claim 1 with an aminooxyalkylate of 1 to 5 units of the compound according to formula (II).

8. A compound as claimed in claim 7, wherein B is a direct bond if A is an esterification product prepared from at least one of the resin compounds mentioned in claim 1 with an aminooxyalkylate of 1 to 3 units of the compound according to formula (II).

9. A compound as claimed in claim 1, wherein
A is the radical of a naturally occurring resin acid, a hydrogenated or disproportionated resin acid or a resin amine or resin alcohol, or the radical of an esterification product which is obtained by esterification of 1 to 6 units of the abovementioned resin acids with a 2- to 6-hydric alcohol, at least one free hydroxyl group being retained.

10. A compound as claimed in claim 9, wherein A is the radical of an esterification product which is obtained by esterification of 1 to 2 units of the abovementioned resin acids with a 2- to 6-hydric alcohol, at least one free hydroxyl group being retained.

11. A compound as claimed in claim 1, wherein
A is an esterification product which is obtained by esterification of 1 to 12 units of a naturally occurring, a hydrogenated or a disproportionated resin acid with an aminooxyalkylate comprising 1 to 5 units of the formula (II), at least one free hydroxyl group being retained.

12. A compound as claimed in claim 11, wherein
A is an esterification product which is obtained by esterification of 1 to 6 units of a naturally occurring, a hydrogenated or a disproportionated resin acid with an aminooxyalkylate comprising 1 to 3 units of the formula (II), at least one free hydroxyl group being retained.

13. A compound as claimed in claim 1, wherein, in formula (I),
m is an integer from 5 to 30.

14. A compound as claimed in claim 1, wherein A is the radical of a commercially available colophony type.

15. A process for the preparation of a compound as claimed in claim 1, which comprises
a1) oxyalkylating naturally occurring resin acids, resin alcohols or resin amines disproportionated or hydrogenated resin acids or esterification products of the resin acids mentioned with polyhydric alcohols, the esterification products still containing at least one free hydroxyl group, with ethylene oxide or propylene oxide or both epoxides in succession or a mixture of both epoxides, 1 to 100 mol of epoxide being employed per reactive hydrogen atom in the resin compound used, or a2) esterifying resin acids mentioned with aminooxyalkylates of the formula (II), b) half-esterifying the products obtained in a1) or a2) on the terminal hydroxyl groups with dicarboxylic acids or dicarboxylic acid anhydrides and c) subsequently converting the free carboxyl groups of the carboxylic acid compound A $[-(B-)_m-CO-F-COOH]_q$ chiefly formed with at least one diamine or polyamine on which the formula Z is based into the particular amide form or salt form.

16. The process as claimed in claim 15, wherein a naturally occurring resin acid, resin alcohol or a resin amine or an esterification product of the resin acids mentioned with a 2- to 6-hydric alcohol is employed as the resin compound, the esterification product still containing at least one free hydroxyl group.

17. The process as claimed in claim 15, wherein an esterification product of a resin acid mentioned in claim 15 with an aminooxyalkylate of the formula (II) is employed as the resin compound, the esterification product still containing at least one free hydroxyl group.

18. The process as claimed in claim 15, wherein the carboxylic acid compound $A[(B)_m-CO-F-COOH]_q$ formed is amidated with at least one amine on which the radical Z is based.

19. The process as claimed in claim 15, wherein the carboxylic acid compound $A[(B)_m-CO-F-COOH]_q$ formed is reacted with at least one amine on which the radical Z is based to give the amine salt.

20. A method for improving the hydrophilicity or surface activity of a material or for improving the surface activity in, or fineness or stability or flow properties of, an emulsification or dispersion, comprising the step of adding a compound of claim 1 to the material or emulsion or dispersion.

21. The method as claimed in claim 20, wherein the improvement in surface activity is manifested as improved corrosion protection, wettability or wetting power, flocculation prevention, leveling properties, dyeing auxiliary properties, coupling auxiliary properties, or metalworking properties.

22. The method as claimed in claim 20, wherein said dispersion is a coloring agent dispersion, and the compound of claim 1 is added as the preparation agent therefor.

23. The method as claimed in claim 21, comprising the step of producing an azo coloring agent for offset printing, said compound of claim 1 being a coupling auxiliary and preparation agent.

* * * * *

UNITED STATES PATENT AND TRADEMARK OFFICE
CERTIFICATE OF CORRECTION

PATENT NO. : 5,266,682
DATED : Nov. 30, 1993
INVENTOR(S) : Heinz Uhrig, et al

It is certified that error appears in the above-indentified patent and that said Letters Patent is hereby corrected as shown below:

At column 1, line 56, "material's" should read --materials--.

At column 2, line 29, the right-hand side of the formula (II)' should read:

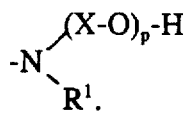

At column 3, line 15, "$R^5$", second occurrence, should read --$R^6$--.

At column 16, line 20, "ailiquarzite" should read --siliquarzite--.

In claim 1, at column 17, line 8, the right-hand side of the formula (II) should read:

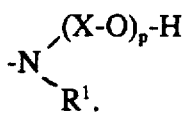

UNITED STATES PATENT AND TRADEMARK OFFICE
CERTIFICATE OF CORRECTION

PATENT NO. : 5,266,682
DATED : Nov. 30, 1993
INVENTOR(S) : Heinz Uhrig, et al

It is certified that error appears in the above-indentified patent and that said Letters Patent is hereby corrected as shown below:

In claim 1, at column 17, line 37, insert "Y" before "is".

In claim 5, at column 18, line 14, insert --1-- before the word "to".

Signed and Sealed this

Twenty-fourth Day of May, 1994

Attest:

BRUCE LEHMAN

Attesting Officer     Commissioner of Patents and Trademarks